United States Patent [19]

Suyama et al.

[11] Patent Number: 5,612,625

[45] Date of Patent: Mar. 18, 1997

[54] METHOD OF MEASURING INNER DIAMETER OF PIPE

[75] Inventors: Kiichi Suyama, Yokohama; Hajime Furusawa, Tokyo; Yasuharu Hosohara; Takashi Kobori, both of Yokohama, all of Japan

[73] Assignee: Tokyo Gas Co., Ltd., Tokyo, Japan

[21] Appl. No.: 544,898

[22] Filed: Oct. 18, 1995

Related U.S. Application Data

[63] Continuation of Ser. No. 230,679, Apr. 21, 1994, abandoned.

[30] Foreign Application Priority Data

Jun. 15, 1993 [JP] Japan ................................. 5-168551

[51] Int. Cl.$^6$ .................................................. G01R 29/00
[52] U.S. Cl. ................................................................ 324/635
[58] Field of Search ....................................... 324/635, 639, 324/644; 73/152.57

[56] References Cited

U.S. PATENT DOCUMENTS

| | | | |
|---|---|---|---|
| 4,109,642 | 8/1978 | Reid | 73/622 |
| 4,689,553 | 8/1987 | Haddox | 324/635 |
| 5,109,699 | 5/1992 | Voruz | 73/632 |

FOREIGN PATENT DOCUMENTS

| | | |
|---|---|---|
| 2434856 | 2/1976 | Germany. |
| 508635 | 8/1972 | U.S.S.R.. |

OTHER PUBLICATIONS

Database WPI, Week 8702 Derwent Publications Ltd., London, GB; AN 87-013644 & SU-A-1 232 943 (Control Prob Inst; Abstract.

Database WPI, Week 8825, Derwent Publications Ltd., London, GB; AN 88-174356 & SU-A-1 355 916 (Gorki Teaching Inst); Abstract.
Patent Abstracts of Japan, vol. 16, No. 562 (P-1456) Dec. 3, 1991 & JP-A-04 215 046 (Nippon Steel Corp) Aug. 5, 1992, Abstract.
H. Mintrop, et al., "Die Anwendung von Mikrowellen zur Prüfung der Innengeometrie von schlanken Stahlrohren", in: Messen und Prüfen/Automatik, No. 10, Oct. 1973. pp. 635–637.
J. C. Gallop, et al., "Dimensional measurement by microwave resonances", in: J. Phys. E: Sci. Instrum. vol. 14, (1981), pp. 461–463.
J. C. Gallop, et al., "Shape and dimensional measurement using microwaves", in: J. Phys. E: Sci. Instrum. 19 (1986), pp. 413–417.

*Primary Examiner*—Christine K. Oda
*Attorney, Agent, or Firm*—Townsend and Townsend and Crew LLP

[57] ABSTRACT

A method of measuring the inner diameter of a pipe includes the steps of continuously transmitting RF waves of a predetermined frequency band from an antenna of a transmitter located inside of the pipe to be inspected, receiving the RF waves with an antenna of a receiver located inside the pipe, the antenna of the receiver being spaced apart from the antenna of the transmitter by a predetermined distance, detecting a frequency at a change point where an intensity of the received RF wave changes greatly, and substituting the frequency at the change point into a formula: $d=c/1.706f$ (wherein d is the inner diameter of the pipe, c is the velocity of light, and f is the frequency at the change point) which shows the relation between the inner diameter of the pipe and the frequency to obtain a minimum inner diameter of the pipe.

5 Claims, 2 Drawing Sheets

METHOD OF MEASURING INNER DIAMETER OF PIPE

This is a continuation application Ser. No. 08/230,679, filed Apr. 21, 1994, now abandoned.

BACKGROUND OF THE INVENTION

1. Field of the Invention

The present invention relates to a method of easily measuring the inner diameter of a pipe such as a gas pipe buried underground within a short period of time.

2. Description of the Relevant Arts

Known conventional methods of measuring the inner diameter of a gas pipe buried underground and inspecting whether a foreign substance such as earth and sand enters into piping include a method of inserting an inspection camera into the pipe to pick up the internal state of the pipe and observe the resultant image, thereby determining the internal state, or using an elastically deformable probe and inserting the probe into the pipe to detect the deformed state of the probe, thereby measuring the inner diameter of the pipe (Japanese Patent Publication No. SHO 57-34482) and a method of radiating a laser beam on the inner wall surface of a pipe and receiving a beam reflected by the inner wall surface to measure the inner diameter (Japanese Patent Laid-Open No. HEI 3-261806).

In the above methods, it is difficult to insert the camera, the probe, and an apparatus for radiating the laser beam and receiving the reflected beam in the pipe so as to conform to the complicated bent shape of the pipe, and the internal state of the pipe cannot be properly inspected. In addition, an insertion hole is required to insert the above inspecting means. To inspect the buried pipe, cumbersome, time-consuming construction work such as digging is be involved. In addition, the inspection distance per cycle is limited to the length of a cable or the like connected to the camera or probe. When inspection is required for a long distance, the number of inspection cycles are undesirably increased, requiring much labor and high cost.

SUMMARY OF THE INVENTION

The present invention has been made in consideration of the above situation, and has as its object to provide a method of measuring the inner diameter of a pipe, which is capable of easily, properly and quickly measuring the inner diameter of the pipe such as a gas pipe buried underground.

In order to achieve the above object, according to the main aspect of the present invention, there is provided a method of measuring an inner diameter of a pipe, including the steps of continuously transmitting radio frequency (RF) waves in a predetermined frequency band from an antenna of a transmitter located inside of the pipe to be inspected, receiving the RF waves by an antenna of a receiver located inside the pipe, the antenna of the receiver being spaced apart from the antenna of the transmitter by a predetermined distance, detecting a frequency at a change point where an intensity of the received RF wave changes greatly, and substituting the frequency at the change point into a formula: $d=c/1{,}706f$ (where d is the diameter of said pipe, c is the velocity of light, and f is the frequency of said change point) which shows the relation between the inner diameter of the pipe and the frequency to obtain a minimum inner diameter of the pipe.

According to a first subsidiary aspect of the present invention, there is provided a method of measuring an inner diameter of a pipe in the method of the main aspect, further comprising the step of comparing the obtained minimum inner diameter and an original inner diameter of the pipe so as to detect the presence/absence of a foreign matter in the pipe or a constricted state in the pipe.

According to a second subsidiary aspect of the present invention, there is provided a method of measuring an inner diameter of a pipe in the method of the main aspect, further comprising the step of comparing the frequency of the change point with predetermined frequency ranges determined for gas pipes having different diameters, thereby estimating the inner diameter of the pipe.

According to a third subsidiary aspect of the present invention, there is provided a method of measuring an inner diameter of a pipe in the method of the main aspect, further comprising the step of shifting the predetermined frequency bend of the RF waves transmitted from the transmitter to a higher-frequency band side.

According to a fourth subsidiary aspect of the present invention, there is provided a method of measuring an inner diameter of a pipe in the method of the main aspect, further comprising the step of shifting the predetermined RF band of the electric waves transmitted from the transmitter to a lower-frequency band side.

According to the method of measuring an inner diameter of a pipe of the present invention, a change in intensity of the RF wave transmitted in the pipe and passing through the pipe is obtained. The inner diameter of the pipe is calculated in accordance with the frequency of the change point where the intensity greatly changes. The diameter of a portion having the minimum inner diameter in the inspection portion can be accurately inspected. The original inner diameter of the pipe is compared with the obtained inner diameter to determine the size of a foreign substance located inside the pipe to be inspected or the inner diameters of pipes connected to the pipe to be inspected and having different inner diameters. In addition, a compoundly curned pipe can be easily inspected because RF waves are used, and the inspection distance in each inspection cycle can be relatively long. Therefore, a long pipe can be easily and properly inspected with a relatively by a smaller number of inspection cycles.

The above and many other advantages, features and additional objects of the present invention will become manifest to those versed in the art upon making reference to the following detailed description and accompanying drawings in which preferred structural embodiments incorporating the principles of the present invention are shown by way of illustrative example.

DETAILED DESCRIPTION OF THE PREFERRED EMBODIMENT

A method of measuring the inner diameter of a pipe according to the present invention will be described in detail with reference to a preferred embodiment illustrated in the accompanying drawings.

Figure 1:
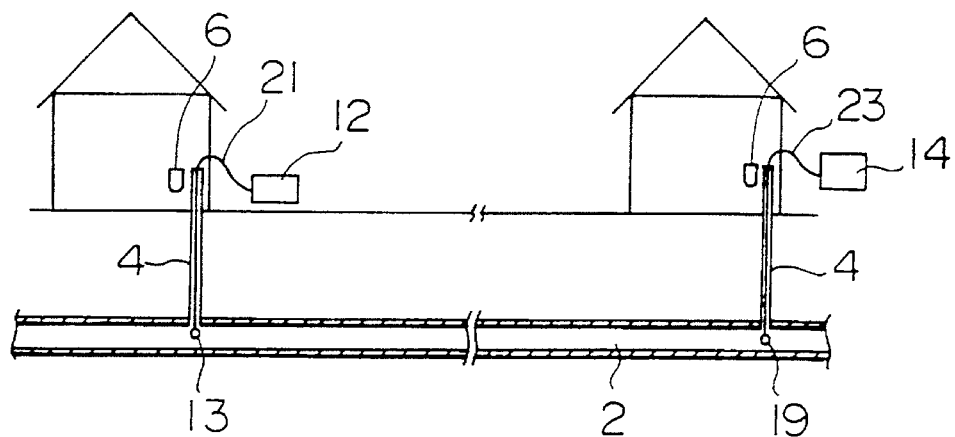
FIG. 1 illustrates an embodiment of a method of measuring the inner diameter of a pipe according to the present invention.

In the following description, assume that a domestic gas pipe buried under a road is measured through a pipe connected to a gas meter installed in each house. A trunk gas pipe 2 buried under a road is combined with domestic gas pipes 4 branching from the trunk gas pipe 2, and meters 6 are respectively mounted at the end portions of the domestic gas pipes 4 to supply the gas therefrom for domestic use, as shown in FIG. 1.

Figure 2:
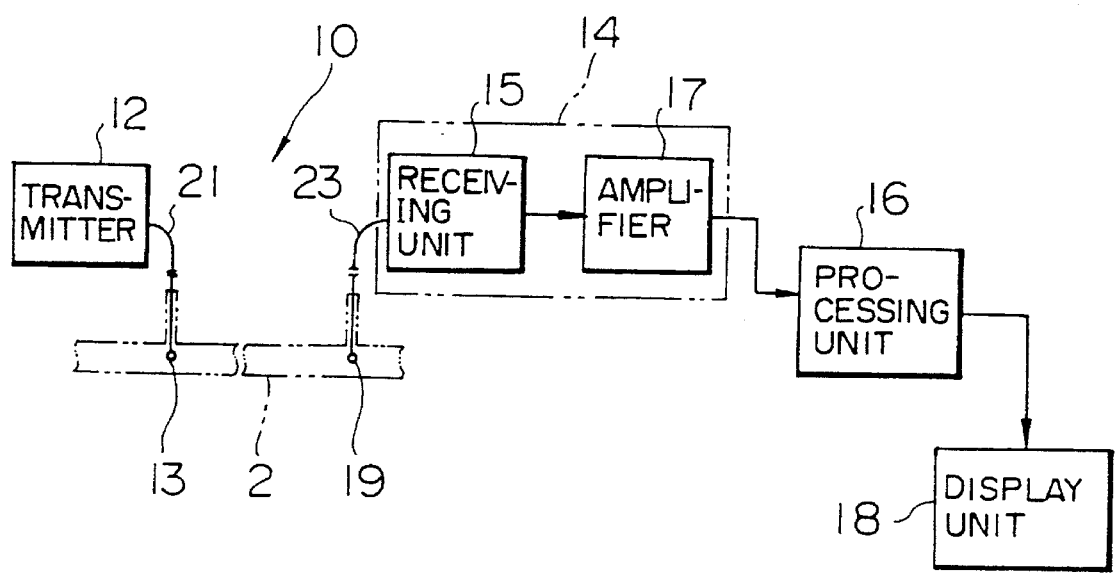
FIG. 2 is a block diagram showing in detail an apparatus used in the method of measuring the inner diameter of a pipe according to the present invention.

Inner pipe diameter measurement is associated with the gas pipe 2, and a measuring apparatus for practicing the inner diameter measuring method of the present invention is shown in FIG. 2. A measuring apparatus 10 comprises a transmitter 12, a receiver 14, a processing unit 16, and a display unit 18. The transmitter 12 can transmit RF waves having a frequency on the order of GHz. A transmission antenna 13 is mounted at the distal end of a lead wire 21. The receiver 14 comprises a receiving unit 15 and an amplifier 17. A reception antenna 19 is mounted to the distal end of a lead wire 23 extending from the receiving unit 15 as in the transmitter 12. Upon reception of the RF waves from the transmitter 12, the received signal is amplified, and the amplified signal is sent to the processing unit 16.

It is known that when RF waves having a frequency higher than the cutoff frequency determined by the inner diameter of a pipe are transmitted inside the pipe, the RF waves reach a remote location without being attenuated inside the pipe. When RF waves are transmitted which include frequencies which can propagate with only little attenuation, the reception intensity abruptly changes with respect to the cutoff frequency as a boundary.

This principle is utilized to analyze RF waves received by the receiver 14 in the processing unit 16. A point where the intensity of the RF waves abruptly changes is detected, and the frequency of this change point is obtained. A substitution of the frequency into the following formula (1), which shows the relation between the inner diameter of the pipe and the frequency, yields the inner diameter of the pipe as follows:

$$d = c/1.706f \qquad (1)$$

where d is the inner diameter of a pipe as an inspection target, c is the velocity of light, and f is the frequency of the change point.

The display unit 18 displays a reception waveform and, at the same time, the frequency of the change point and the inner diameter of the pipe.

Measuring procedures will new be described. Two gas meters 6 which interpose a target inspection portion are selected, and the domestic gas pipes 4 are disconnected from the gas meters 6. The antenna 13 of the transmitter 12 is inserted through an opening of one removed domestic gas pipe 4 and is passed along until the antenna 13 reaches the interior of the trunk gas pipe 2. This operation may be performed after or before the gas supply is interrupted. If the gas supply is not interrupted during the measurement, the openings of the domestic gas pipes 4 are sealed to prevent gas leakage.

The antenna 19 of the receiver 14 is inserted through the opening of the other domestic gas meter 6 until the antenna 19 reaches the interior of the trunk gas pipe 2. In this manner, when the antennas 13 and 19 of the transmitter 12 and the receiver 14 are located on each side of the target inspection portion of the trunk gas pipe 2, RF waves having a predetermined frequency band are transmitted by the transmitter 12. This frequency band includes at least an RF wave having a frequency derived by a formula: $f=c/1.706d$ obtained by developing the foregoing formula (1). For example, if the trunk gas pipe 2 to be inspected is a 100A pipe having an inner diameter of about 105 mm, the predetermined frequency band falls within the range of 1 to 5 GHz.

The RF waves in the predetermined frequency band are continuously and sequentially transmitted by the transmitter, and the RF waves propagating along the trunk gas pipe 2 are received by the antenna 19 of the receiver 14. The received RF waves are amplified, and the amplified waves are sent to the processing unit 16. The reception intensities of the received waves are analyzed to detect the frequency corresponding to a change point where the intensity abruptly changes. When this change point is confirmed, the frequency value of this change point is substituted into the formula (1). In this manner, the minimum inner diameter within the inspection range is readily obtained.

When the inner diameter of the minimum portion is obtained, the original inner diameter of the trunk gas pipe 2 is compared with the inner diameter obtained from the frequency. Any significant difference that is detected between them, indicates that there is a foreign substance which reduces the original inner diameter of the trunk gas pipe 2 to the one that was measured, or that a length of reduce diameter pipe located midway along the trunk gas pipe 2 forms a constriction the pipe.

Gas pipes are generally manufactured in accordance with predetermined standards, and their inner diameters change incrementally and are known in advance. For this reason, if a constriction is detected, the measured frequency may be compared with frequency ranges corresponding to standard pipes having different inner diameters to estimate the inner diameter of the connected pipe. In this manner, frequency ranges may be set for gas pipes having predetermined standards of sizes, respectively, and the diameter of each pipe can be determined on the basis of these frequency ranges. Even if noise is included in received RF waves, the minimum inner diameter of the pipe can be accurately determined without being adversely affected by the noise.

There are two cases in which the intensity of RF waves does not change although the pipe diameter changes. First, this occurs when a predetermined frequency band selected in advance is a relatively low-frequency band, and the detection point is below the change point. Second, this also occurs when a predetermined frequency band selected in advance is a relatively high-frequency band, and the detection point exceeds the change point. In the former case, the frequency band is shifted to a higher frequency to detect the change point. In the latter case, the frequency band is shifted to a lower frequency to detect the change point.

The following are the results of experiments using the above measuring method. In experiment 1, a 100A gas pipe (overall length: 9 m) having an inner diameter of about 105 mm was used. In experiment 2, a 50A gas pipe (overall length: 4.88 m) having an inner diameter of about 52 mm was used. The antennas of the transmitter and the receiver were connected to both ends of each pipe, respectively, and located slightly inside each pipe. RF waves in the frequency range of 0.960 GHz to 6.00 GHz were swept and transmitted, and RF waves propagating through each pipe were received by the receiver. Changes in intensity of received RF waves in experiment 1 are shown in FIG. 3, and those in experiment 2 are shown in FIG. 4.

Figure 3:
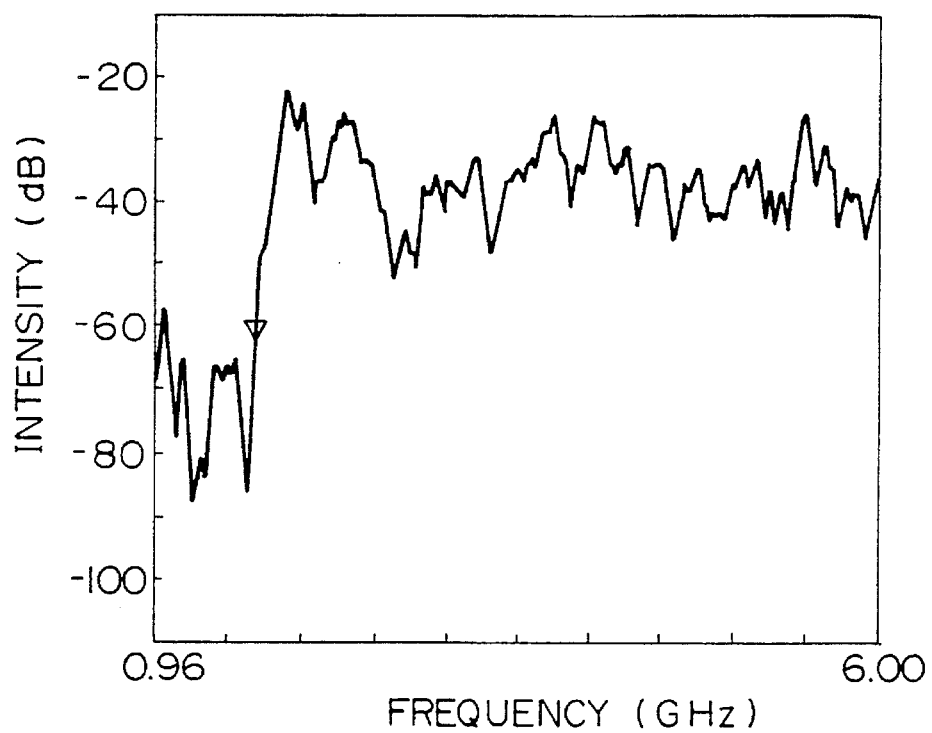
FIGS. 3 and 4 are graphs showing experimental results of the method of measuring the inner diameter of a pipe according to the present invention.
Figure 4:
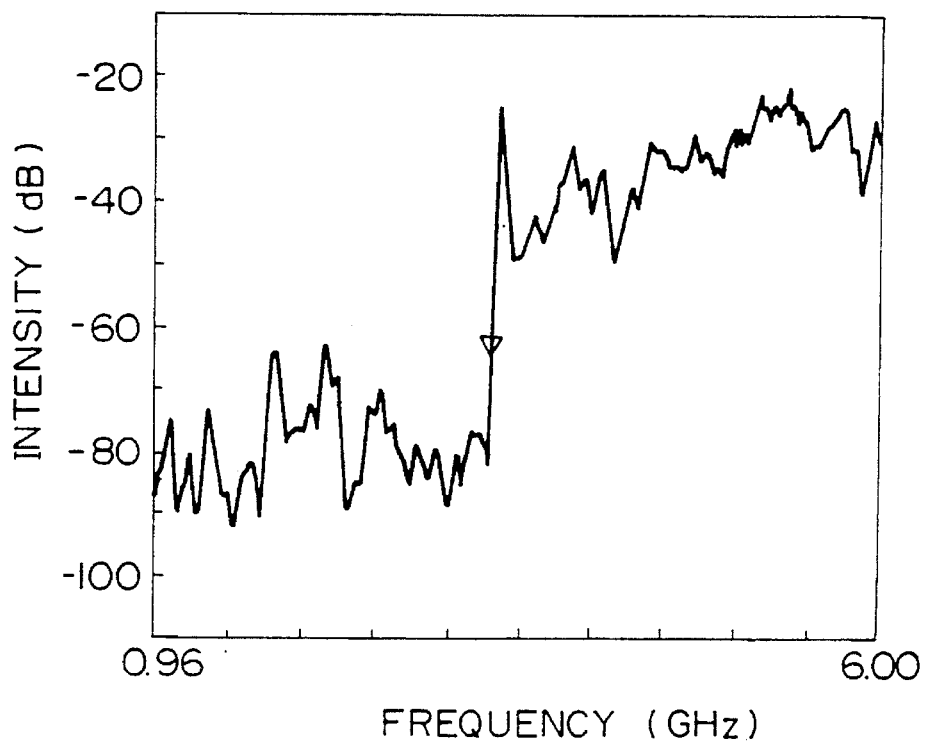

In experiment 1, the change point of the reception intensity is apparently 1.6665 GHz from the graph in FIG. 3, and roughly agrees with the frequency of 1.6704 GHz for a pipe having an inner diameter of about 105 mm obtained by the formula (1). Similarly in experiment 2 the change point of the reception intensity is apparently 3.2959 GHz from the graph in FIG. 4, and roughly agrees with the frequency of 3.3251 GHz for a pipe having the inner diameter of about 52 mm obtained by the formula (1).

As has been described above, the antennas 13 and 19 of the transmitter 12 and the receiver 14 are respectively inserted from the mounting portions of the two domestic gas meters 6 spaced apart from each other and are passed to the trunk gas pipe 2 to be inspected. Changes in reception intensity of the RF waves transmitted from the transmitter 12 are observed, and the inner diameter of the pipe is calculated in accordance with the frequency corresponding to the point where the intensity greatly changes. The inner diameter of the most constricted portion of the trunk gas pipe 2 from the transmission antenna 13 to the reception antenna 19 can be accurately measured. The original inner diameter of the trunk gas pipe 2 is compared with the inner diameter obtained by the formula (1) to obtain a difference, thereby determining the size of a foreign substance present in the trunk gas pipe 2 or the inner diameter of a small-diameter pipe connected midway along the trunk gas pipe 2. In addition, the inspection distance can be increased because RF waves are used. The trunk gas pipe 2 having a large length can be inspected by a smaller number of inspection cycles. Even if the trunk gas pipe 2 is compoundly curved, the RF waves attenuate little to facilitate accurate inspection.

The above embodiment has exemplified a gas pipe as an inspection target object. However, the measuring method of the present invention is not limited to application to the gas pipe.

In addition, in the above embodiment, the antenna 13 or the like is inserted from the connection port of the corresponding gas meter 6. However, insertion of the antenna 13 or the like is not limited to this method. The antennas may be inserted from other locations if they can reach two points if they are located within the range over which the RF waves are effective.

What is claimed is:

1. A method of measuring an inner diameter of a pipe, comprising the steps of continuously transmitting RF waves of a predetermined frequency band from an antenna of a transmitter located inside of the pipe to be inspected, receiving the RF waves with an antenna of a receiver located inside the pipe, said antenna of the receiver being spaced apart from said antenna of the transmitter by a predetermined distance, detecting a frequency at a change point where an intensity of the received RF wave changes greatly, substituting the frequency at the change point into a formula: $d=c/1.706f$ wherein d is the diameter of said pipe, c is the velocity of light, and f is the frequency at said change point) which shows the relation between the inner diameter of the pipe and the frequency to obtain a minimum inner diameter of the pipe.

2. A method according to claim 1, further comprising the step of comparing the obtained minimum inner diameter and an original inner diameter of the pipe so as to detect at least one of foreign matter in the pipe and a constriction in the pipe.

3. A method according to claim 1, further comprising the step of comparing the frequency at the change point with predetermined frequency ranges determined for gas pipes having different diameter, and therewith estimating the inner diameter of the pipe.

4. A method according to claim 1, further comprising the step of shifting the predetermined frequency band of the RF waves transmitted from the transmitter to a higher-frequency band side.

5. A method according to claim 1, further comprising the step of shifting the predetermined frequency band of the RF waves transmitted from the transmitter to a lower-frequency band side.

* * * * *